(12) United States Patent
Giovannini et al.

(10) Patent No.: US 8,148,405 B2
(45) Date of Patent: Apr. 3, 2012

(54) SALT I (75) Inventors: Julien Giovannini, Loughborough (GB); Bo-Goran Josefsson, Lund (SE)

(73) Assignee: AstraZeneca AB, Södertälje (SE)

( * ) Notice: Subject to any disclaimer, the term of this patent is extended or adjusted under 35 U.S.C. 154(b) by 1090 days.

(21) Appl. No.: 11/997,500

(22) PCT Filed: Jul. 31, 2006

(86) PCT No.: PCT/SE2006/000920
§ 371 (c)(1),
(2), (4) Date: Jan. 31, 2008

(87) PCT Pub. No.: WO2007/015666
PCT Pub. Date: Feb. 8, 2007

(65) Prior Publication Data
US 2008/0227817 A1    Sep. 18, 2008

(30) Foreign Application Priority Data

Aug. 2, 2005  (SE) ..................... 0501768

(51) Int. Cl.
*A61K 31/4468*  (2006.01)
*C07D 211/58*   (2006.01)
(52) U.S. Cl. ........................ 514/329; 546/224
(58) Field of Classification Search .......... 514/329; 546/223
See application file for complete search history.

(56) References Cited

U.S. PATENT DOCUMENTS

| 3,203,992 A | 8/1965 | Kunz et al. |
| 3,577,432 A | 5/1971 | Helsley et al. |
| 3,755,584 A | 8/1973 | Plotnikoff et al. |
| 3,818,017 A | 6/1974 | Janssen et al. |
| 3,894,030 A | 7/1975 | Janssen et al. |
| 3,929,768 A | 12/1975 | Brattsand et al. |
| 3,994,974 A | 11/1976 | Murakami et al. |
| 4,029,801 A | 6/1977 | Cavalla et al. |
| 4,080,328 A | 3/1978 | Maruyama et al. |
| 4,166,119 A | 8/1979 | Effland et al. |
| 4,264,613 A | 4/1981 | Regnier et al. |
| 4,304,915 A | 12/1981 | Berthold |
| 4,338,323 A | 7/1982 | Regnier et al. |
| 4,579,854 A | 4/1986 | Iwakuma et al. |
| 5,576,321 A | 11/1996 | Krushinski, Jr. et al. |
| 5,614,523 A | 3/1997 | Audia et al. |
| 5,614,533 A | 3/1997 | Anderson et al. |
| 5,627,196 A | 5/1997 | Audia et al. |
| 5,741,789 A | 4/1998 | Hibschman et al. |

(Continued)

FOREIGN PATENT DOCUMENTS
DE   2323215   11/1973
(Continued)

OTHER PUBLICATIONS

Braga et al. "Making crystals . . . " Roy. Soc. Chem. Chem. Commun. p. 3635-3645 (2005).*

(Continued)

*Primary Examiner* — Celia Chang
(74) *Attorney, Agent, or Firm* — Fish & Richardson P.C.

(57)  ABSTRACT

The invention provides N-{2-[((2S)-3-{[1-(4-chlorobenzyl) piperidin-4-yl]amino}-2-hydroxy-2-methylpropyl)oxy]-4-hydroxyphenyl}acetamide benzoate or a solvate thereof, pharmaceutical compositions containing the salt or solvate and use of the salt or solvate in therapy.

16 Claims, 4 Drawing Sheets

U.S. PATENT DOCUMENTS

| | | | |
|---|---|---|---|
| 5,789,402 A | 8/1998 | Audia et al. | |
| 6,518,286 B1 | 2/2003 | Baxter et al. | |
| 6,911,458 B2* | 6/2005 | Eriksson et al. | 514/329 |
| 6,927,222 B2 | 8/2005 | Hansen et al. | |
| 6,943,188 B2 | 9/2005 | Bodkin et al. | |
| 6,951,874 B2 | 10/2005 | Hansen et al. | |
| 7,005,439 B2 | 2/2006 | Eriksson et al. | |
| 7,345,063 B2 | 3/2008 | Eriksson et al. | |
| 7,388,020 B2 | 6/2008 | Eriksson et al. | |
| 7,528,156 B2* | 5/2009 | Eriksson et al. | 514/329 |
| 2003/0055080 A1 | 3/2003 | Forner et al. | |
| 2005/0239801 A1 | 10/2005 | Eriksson et al. | |
| 2008/0176902 A1 | 7/2008 | Giovannini et al. | |
| 2008/0194632 A1 | 8/2008 | Giovannini et al. | |
| 2008/0280951 A1 | 11/2008 | Giovannini et al. | |
| 2009/0215732 A1 | 8/2009 | Eriksson et al. | |
| 2009/0298875 A1 | 12/2009 | Eriksson et al. | |
| 2009/0306141 A1 | 12/2009 | Eriksson et al. | |
| 2010/0041905 A1 | 2/2010 | Ainge et al. | |
| 2010/0081692 A1 | 4/2010 | Hemmerling et al. | |

FOREIGN PATENT DOCUMENTS

| | | |
|---|---|---|
| DE | 3723648 | 1/1989 |
| DE | 4129535 | 3/1992 |
| DE | 19703131 | 7/1998 |
| DE | 19755268 | 6/1999 |
| EP | 0095454 | 11/1983 |
| EP | 0128007 | 12/1984 |
| EP | 0496691 | 7/1992 |
| EP | 0587311 | 3/1994 |
| EP | 0722941 | 7/1996 |
| EP | 0903349 | 3/1999 |
| EP | 1389616 | 2/2004 |
| EP | 1263724 | 5/2005 |
| FR | 2190430 | 2/1974 |
| GB | 1368012 | 9/1974 |
| GB | 2373186 | 9/2002 |
| WO | WO 92/05147 | 4/1992 |
| WO | WO 93/25528 | 12/1993 |
| WO | WO 97/22596 | 6/1997 |
| WO | WO 97/23458 | 7/1997 |
| WO | WO 97/30035 | 8/1997 |
| WO | WO 97/32856 | 9/1997 |
| WO | WO 98/13354 | 4/1998 |
| WO | WO 98/32442 | 7/1998 |
| WO | WO 99/02166 | 1/1999 |
| WO | WO 99/25686 | 5/1999 |
| WO | WO 99/31092 | 6/1999 |
| WO | WO 99/65895 | 12/1999 |
| WO | WO 00/31033 A1 | 6/2000 |
| WO | WO 00/35449 | 6/2000 |
| WO | WO 00/35451 | 6/2000 |
| WO | WO 00/40529 | 7/2000 |
| WO | WO 00/41669 | 7/2000 |
| WO | WO 00/53187 | 9/2000 |
| WO | WO 00/53600 | 9/2000 |
| WO | WO 00/58305 | 10/2000 |
| WO | WO 00/69820 | 11/2000 |
| WO | WO 00/75114 | 12/2000 |
| WO | WO 01/14333 | 3/2001 |
| WO | WO 01/43744 | 6/2001 |
| WO | WO 01/44227 | 6/2001 |
| WO | WO 01/62728 A1 | 8/2001 |
| WO | WO 01/62729 A1 | 8/2001 |
| WO | WO 01/62757 A1 | 8/2001 |
| WO | WO 01/87839 A1 | 11/2001 |
| WO | WO 01/89492 A1 | 11/2001 |
| WO | WO 01/92224 | 12/2001 |
| WO | WO 01/98270 | 12/2001 |
| WO | WO 01/98272 A1 | 12/2001 |
| WO | WO 01/98273 A1 | 12/2001 |
| WO | WO 02/00679 | 1/2002 |
| WO | WO 02/04434 | 1/2002 |
| WO | WO 02/08213 | 1/2002 |
| WO | WO 02/12265 | 2/2002 |
| WO | WO 02/12266 | 2/2002 |
| WO | WO 02/20484 A1 | 3/2002 |
| WO | WO 02/45703 | 6/2002 |
| WO | WO 02/074763 | 9/2002 |
| WO | WO 02/076457 | 10/2002 |
| WO | WO 02/076933 | 10/2002 |
| WO | WO 02/076948 | 10/2002 |
| WO | WO 02/079156 | 10/2002 |
| WO | WO 02/088167 | 11/2002 |
| WO | WO 03/042164 | 5/2003 |
| WO | WO 03/042178 | 5/2003 |
| WO | WO 03/051839 A1 | 6/2003 |
| WO | WO 03/068743 A1 | 8/2003 |
| WO | WO 03/080574 | 10/2003 |
| WO | WO 03/082292 | 10/2003 |
| WO | WO 2004/032921 | 4/2004 |
| WO | WO 2005/010154 | 2/2005 |
| WO | WO 2005/025555 | 3/2005 |
| WO | WO 2005/041980 | 5/2005 |
| WO | WO 2007/015664 | 2/2007 |
| WO | WO 2007/015666 | 2/2007 |
| WO | WO 2007/015667 | 2/2007 |
| WO | WO 2007/015668 | 2/2007 |
| WO | WO 2007/024182 | 3/2007 |
| WO | WO 2007/024183 | 3/2007 |
| WO | WO 2007/053082 | 5/2007 |
| WO | WO 2007/129960 | 11/2007 |
| WO | WO 2008/010764 | 1/2008 |
| WO | WO 2008/103125 | 8/2008 |

OTHER PUBLICATIONS

Cohen et al. "Cytokine function" Am. J. Clin. Path. 105(5)589-598 (1996).*
Horuk et al. "CCR1 specific . . . " Immunology Lett 76 p. 193-201 (2001).*
Lee et al. "CCR1 mediated . . . " J. Leukocyte Biol. v.86 p. 1319-1329 (2009).*
Seddon "pseudopolymorph . . . " Crystal growth and design 496) 1087 (2004) (2 pages from internet).*
Berge "Pharmaceutical salts" j. pharm. sci. p. 1-19 (1977).*
Dean "Analytical chemistry handbook" p. 10.24-10.26 (1995).*
Brittain "Polymorphism in phaarm . . . " p. 236 (1999).*
Aldridge "The shape shifter" Chemistry World , p. 64-70 (2007).*
Alcaraz et al., "Preparation of piperidinyl alcohols as chemokine receptor modulators for treatment of diseases such as asthma", CAPLUS 139:197375 (2003).
Archibald et al., "Antiinflammatory 4-acylaminopiperidines", CAPLUS 77:34355 (1972).
Barnes et al., "COPD: is there light at the end of the tunnel?", Curr Opin Pharmacol 4:263-272 (2004).
Barnes et al., "Prospects for new drugs for chronic obstructive pulmonary", Lancet 364:985-996 (2004).
Bechtloff et al., "Pseudopolymorphs in industrial use", SciSearch 10289666 (2001).
Berthold, "3-Aminopropoxyaryl derivatives", CAPLUS 93:8015 (1980).
Black et al., "Increased chemical purity using a hydrate", SciSearch 12765805 (2004).
Blease et al., "Emerging treatments for asthma", Expert Opin. Emerging Drugs 8:71-81 (2003).
Cattanach et al., "Studies in the Indole Series. Part IV. Tetrahydro-1H-pyrido[4, 3-b]-indoles as Serotonin Antagonists", J. Chem. Soc. C. 10:1235-1243 (1968).
Chou et al., "Adrenergic regulation of macrophage-derived tumor necrosis factor-α generation during a chronic polyarthritis pain model", CAPLUS 129:3784 (1998).
de Boer, "Potential new drugs for therapy of chronic obstructive pulmonary disease", Expert Opin. Investig. Drugs 12:1067-1086 (2003).
Edenhofer et al., "Hypotensive aromatic ethers and their pharmaceutical compositions", CAPLUS 73:87939 (1970).
Eriksson et al., "Preparation of benzimidazol derivatives as modulators of chemokine receptors", CAPLUS 137:247698 (2002).
Eriksson et al., "Preparation of substituted 1-benzyl-4-piperidinamines as chemokine receptor modulators", CAPLUS 136:69740 (2001).

Exhibit A CAS search result.
Finlayson et al., "Acquired QT interval prolongation and HERG: implications for drug discovery and development", *Eur. J Pharm.* 500:129-142 (2004).
Friebe et al., "Piperidinopropyl derivatives and pharmaceutical compositions containing them", *CAPLUS* 94:103172 (1981).
García-Marcos et al., "Inhaled corticosteroids plus long-acting $\beta_2$-agonists as a combined therapy in asthma", *Expert Opin. Pharmacother.* 4:23-39 (2003).
Guillaumel et al., "Recherches sur les dérivés nitrés d'intérêt biologique", *Eur. J. Med. Chem.* 18(5):431-436 (1983).
Hansen et al., "Preparation of substituted 1-phenoxy-3-pyrrolidino (or piperidino)propan-2-ols as chemokine receptor modulators", *CAPLUS* 135:195501 (2001).
Haverkamp et al., "The potential for QT prolongation and proarrhythmia by non-antiarrhythmic drugs: clinical and regulatory implications", *Eur Heart J* 21:1216-1231 (2000).
Hesselgesser et al., "Identification and Characterization of Small Molecule Functional Antagonists of the CCR1 Chemokine Receptor", *J. Biol. Chem.* 273(25):15687-15692 (1998).
Hoffman, Chapter 10 "Catecholamines, Sympathomimetic Drugs, and Adrenergic Receptor Antagonists, Goodman & Gilman's The Pharmacological Basis of Therapeutics, $10^{th}$ ed. "Hardman JG, Limbird LE, and Gilman AG, Eds., McGraw-Hill, 2001, 215-268 (pp. 215, 230, and 231 provided).
Howard et al., "Chemokines: progress toward identifying molecular targets for therapeutic agents", *Trends in Biotechnology* 14:46-51 (1996).
Hu et al., "Dependence of the chemical dynamics of intercluster association reactions on the strength of the solute-solvent intermolecular potential", *Beilstein Abs.* 5809171 (1993).
Katritzky et al., "Heterocyclic Chemistry", Cambridge, p. 75 (1964).
Kirk-Othmer, "Crystallization" in: *Encyclopedia of Chemical Technology*(2002 ed.), pp. 95-147.
Kiss et al., "High Throughput Ion-Channel Pharmacology: Planar-Array-Based Voltage Clamp", *Assay Drug Dev. Technol.* 127-135 (2003).
Manabu Hori Kim D. Janda, "A Soluble Polymer Approach to the "Fishing Out" Principle: Synthesis and Purification of β-Amino Alcohols", *J. Org. Chem.* 63:889-894 (1998).
Komai et al., "Structure-Activity Relationships of HIV-1 PR Inhibitors Containing AHPBA-II. Modification of Pyrrolidine Ring at P1' Proline", *Bioorganic & Medicinal Chemistry* 4(8):1365-1377 (1996).
Leclerc et al., "Derivatives Related to Betaxolol with I- and J-Adrenergic Activities", *Arzneim.-Forsch/Drug. Res.* 35(11):1357-1367 (1985).
Levine, "β2-Andrenergic mechanisms in experimental arthritis", *CAPLUS* 109:52680 (1988).
Matsuo et al., "Preparation of N-pentadienoylaminoalkyl-4-(3-indolyl) piperidines and analogs as antiallergic agents", *CAPLUS* 115:232091 (1991).
Meurer et al., "Discovery of potent human CCR5 antagonists for the treatment of HIV-1 infection—II.", *CAPLUS* 2000:331722 (2000).
Mirzadegan et al., "Identification of the Binding Site for a Novel Class of CCR2b Chemokine Receptor Antagonists", *J. Biol. Chem.* 275(33):25562-25571 (2000).
Mizuhashi, "A guinea pig model of propranolol-induced bronchoconstriction (PIB) after allergic immediate asthmatic reaction and the role of thromboxane A2 and 5-lipoxygenase products", *CAPLUS* 122:71729 (1995).
Navas III et al., "The Design and Synthesis of a Hapten for 1192U90, A Potential Atypical Antipsychotic Agent", *Synthetic Communications* 26(7):1411-1421 (1996).

Payard et al., "N-Aminomethylated Derivatives of Some Hydroxamic Acids as Anti-Inflammatories", *Eur. J. Med. Chem.* pp. 1-10 (1975).
Rollins, "Chemokines", *Blood* 90 (3):909-928 (1997).
Rubini et al., "Synthesis of Isosteric Methylene-Oxy Pseudodipeptide Analogues as Novel Amide Bond Surrogate Units", *Tetrahedron* 42(21):6039-6045 (1986).
Saeki et al., "CCR1 Chemokine Receptor Antagonist", *Current Pharmaceutical Design* 9:1201-1208 (2003).
Saeki, "Molecular mechanism of rheumatoid arthritis and relationship between cytokine and chronic rheumatoid arthritis", *CAPLUS* 125:272100 (1996).
Sanguinetti et al., "A Mechanistic Link between an Inherited and an Acquired Cardiac Arrhythmia: *HERG* Encodes the $I_{Kr}$ Potassium Channel", *Cell* 81:299-307 (1995).
Schmidt et al., "Molecular mechanisms in allergy and clinical immunology", *J Allergy Clin Immunol* 105:673-682 (2000).
STN International, File CAPLUS, CAPLUS Accession No. 1968:402884.
Tanabe et al., "Propanol derivatives as antihypertensives", *CAPLUS* 96:110143 (1982).
Tanaka et al., "Antiallergic effects of a novel compound, SWR-00151", *CAPLUS* 126:311929 (1997).
Thalén and Brattsand, "Synthesis and Anti-inflammatory Properties of Budesonide, a New Non-halogenated Glucocorticoid with High Local Activity", *Arzneim.-Forsch./Drug Res.* 29(II):1687-1690 (1979).
Timmermans et al., "Hypotensive Properties of Benzodioxane Derivatives Structurally Related to R 28935. Comparison of Activity with some Receptor Affinities", *Arch. int. Pharmacodyn.* 255:321-334 (1982).
Tomlinson et al., "Efficacy of low and high dose inhaled corticosteroid in smokers versus non-smokers with mild asthma", *Thorax* 60:282-287 (2005).
Wright et al., "Discovery of Selective Dopamine D4 Receptor Antagonists: 1-Aryloxy-3-(4-Aryloxypiperidinyl)-2-Propanols", *Bioorganic & Medicinal Chemistry Letters* 7(11):1377-1380 (1997).
Wright et al., "Subtype-Selective N-Methyl-D-Aspartate Receptor Antagonists: Synthesis and Biological Evaluation of 1-(Heteroarylalkynl)-4-benzylpiperidines", *CAPLUS* 133:321781 (2000).
Yamamoto, "Expression of monocyte chemotactic activity by cross-linked dimerization of a ribosomal protein", *CAPLUS* 127:64176 (1997).
Zenitz et al., "3-(Piperidino-lower-alkyl) indoles", *CAPLUS* 87:102164 (1977).
Zhou et al., "α-Aminothiazole-γ-aminobutanoic amides as potent, small molecule CCR2 receptor antagonists", *Bioorganic & Medicinal Chemistry Letters* 17:309-314 (2007).
USPTO Restriction Requirement in U.S. Appl. No. 12/434,955, mailed May 19, 2011, 5 pages.
USPTO Non-Final Office Action in U.S. Appl. No. 11/997,513, mailed Feb. 28, 2011, 10 pages.
USPTO Non-Final Office Action in U.S. Appl. No. 11/997,489, mailed Feb. 25, 2011, 12 pages.
USPTO Non-Final Office Action in U.S. Appl. No. 11/997,474, mailed Feb. 28, 2011, 12 pages.
USPTO Restriction Requirement in U.S. Appl. No. 12/064,864, mailed Jan. 27, 2011, 10 pages.
Fish & Richardson P.C., Response to Restriction Requirement of Jan. 27, 2011 in U.S. Appl. No. 12/064,864, filed Feb. 23, 2011, 2 pages.
USPTO Non-Final Office Action in U.S. Appl. No. 12/064,864, mailed Mar. 30, 2011, 12 pages.

* cited by examiner

SALT I

CROSS-REFERENCE TO RELATED APPLICATIONS

This application is a national phase application under 35 U.S.C. §371 of PCT International Application No. PCT/SE2006/000920, filed Jul. 31, 2006, which claims the benefit of Swedish Application Serial No. 0501768-6, filed Aug. 2, 2005. Each of these prior applications is incorporated herein by reference in its entirety.

The present invention relates to a salt of a piperidine derivative, pharmaceutical composition containing it and its use in therapy.

Chemokine Receptor 1 (CCR1) is highly expressed in tissues affected in different autoimmune, inflammatory, proliferative, hyper proliferative and immunologically mediated diseases, e.g. asthma, chronic obstructive pulmonary disease, multiple sclerosis and rheumatoid arthritis. Therefore, inhibiting CCR1-mediated events with the salt of the invention, e.g. by cell activation and migration, is expected to be effective in the treatment of such conditions.

In the manufacture of pharmaceutical formulations, it is important that the active compound is in a form in which it can be conveniently handled and processed in order to obtain a commercially-viable manufacturing process. In this connection, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

Furthermore, if the active compound is to be incorporated into a formulation for pulmonary administration, e.g., via a dry powder inhaler such as the Turbuhaler® device, it is desirable if the active compound can be readily micronised to yield a powder with good flow properties and comprising a high fine crystalline particle fraction (i.e. a fraction in which the active compound particles have a mass median aerodynamic diameter of less than 10 μm (micrometer)). Such a fraction is capable of being carried deep into the lungs leading to faster and increased absorption of the active compound.

International Patent Application Publication No. WO 03/051839 generally discloses certain piperidinyl derivatives that have activity as CCR1 antagonists and, in particular, the compound 4-({(2S)-3-[2-(acetylamino)-5-hydroxyphenoxy]-2-hydroxy-2-methylpropyl}ammonio)-1-(4-chlorobenzyl)piperidine and pharmaceutically acceptable salts or solvates thereof. The only salt of this compound specifically disclosed in the application is the ditrifluoroacetate salt, which being amorphous in character, does not make it suitable for use in a dry powder formulation for pulmonary administration.

It has now surprisingly been found possible to prepare a salt of the compound 4-({(2S)-3-[2-(acetylamino)-5-hydroxyphenoxy]-2-hydroxy-2-methylpropyl}ammonio)-1-(4-chlorobenzyl)piperidine having good physico-chemical properties which is capable of being formulated in a dry powder formulation for pulmonary administration.

The structure of 4-({(2S)-3-[2-(acetylamino)-5-hydroxyphenoxy]-2-hydroxy-2-methylpropyl}ammonio)-1-(4-chlorobenzyl)piperidine is shown below:

Thus, in accordance with the present invention, there is provided the benzoate salt of 4-({(2S)-3-[2-(acetylamino)-5-hydroxyphenoxy]-2-hydroxy-2-methylpropyl}ammonio)-1-(4-chlorobenzyl)piperidine (hereinafter referred to as N-{2-[((2S)-3-{[1-(4-chlorobenzyl)piperidin-4-yl]amino}-2-hydroxy-2-methylpropyl)oxy]-4-hydroxyphenyl}acetamide benzoate, "the benzoate salt").

The invention also provides solvates (including hydrates) of the benzoate salt. However, the benzoate salt is preferably anhydrous, and preferably in non-solvated form.

In an embodiment of the invention, the benzoate salt or solvate thereof has crystalline properties and is preferably at least 50% crystalline, more preferably at least 60% crystalline, still more preferably at least 70% crystalline and most preferably at least 80% crystalline. Crystallinity can be estimated by conventional X-ray diffractometry techniques.

In another embodiment of the invention, the benzoate salt or solvate thereof is from 50%, 60%, 70%, 80% or 90% to 95%, 96%, 97%, 98%, 99% or 100% crystalline.

Without being bound to any particular theory, the benzoate salt is believed to be polymorphic and two forms have been isolated and characterised to date.

One polymorph (hereinafter referred to as Form A) exhibits at least the following characteristic X-ray powder diffraction (XRPD) peaks (expressed in degrees 2θ) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25th ed. Rockville, Md.: United States Pharmacopeial Convention; 2002: 2088-2089):

(1) 6.1, 10.7 and 19.3, or
(2) 6.1, 12.2 and 14.1, or
(3) 6.1, 10.7, 12.2, 14.1, 18.1 and 19.3, or
(4) 6.1, 10.7, 12.2, 14.1, 15.7, 18.1 and 19.3, or
(5) 6.1, 10.7, 12.2, 14.1, 15.1 and 19.3, or
(6) 6.1, 10.7, 12.2, 14.1, 15.1, 15.7, 18.1 and 19.3, or
(7) 6.1, 10.7, 12.2, 14.1, 15.1, 15.7, 18.1, 19.3, 21.2 and 24.6.

Form A may be prepared substantially free of other physical forms by a process comprising the following steps:

(i) contacting a heated solution of N-{2-[((2S)-3-{[1-(4-chlorobenzyl)piperidin-4-yl]amino}-2-hydroxy-2-methylpropyl)oxy]-4-hydroxyphenyl}acetamide dissolved in a suitable solvent or mixture of solvents (e.g. an organic solvent such as a polar solvent, examples of which include methanol, ethanol, n-propanol, isopropanol, acetone and ethyl acetate), with (ii) a heated solution of benzoic acid dissolved in a suitable solvent or mixture of solvents (e.g. an organic solvent such as a polar solvent, examples of which include methanol, ethanol, n-propanol, isopropanol, acetone and ethyl acetate), to obtain a mixture, (iii) allowing the mixture to cool to ambient temperature (e.g. 20° C.) to yield a precipitate of Form A of N-{2-[((2S)-3-{[1-(4-chlorobenzyl)piperidin-4-yl]amino}-2-hydroxy-2-methylpropyl)oxy]-4-hydroxyphenyl}acetamide benzoate, and (iv) separating the precipitate from the mixture.

The other polymorph (hereinafter referred to as Form B) exhibits at least the following characteristic X-ray powder diffraction (XRPD) peaks (expressed in degrees 2θ) (the margin of error being consistent with the United States Pharmacopeia general chapter on X-ray diffraction (USP941)—see the United States Pharmacopeia Convention. X-Ray Diffraction, General Test <941>. *United States Pharmacopeia*, 25th ed. Rockville, Md.: United States Pharmacopeial Convention; 2002:2088-2089):

(1) 6.5, 9.3 and 10.5, or
(2) 6.5, 9.3, 17.6 and 17.8, or
(3) 6.5, 9.3, 10.5, 12.0 and 12.4, or
(4) 6.5, 9.3, 10.5, 12.0, 12.4, 13.0, 13.6, 15.5, 17.6 and 17.8, or
(5) 6.5, 13.0 and 20.2, or
(6) 6.5, 9.3, 10.5, 12.0, 12.4, 13.0, 13.6, 15.5, 17.6, 17.8 and 19.2, or
(7) 6.5, 9.3, 10.5, 12.0, 12.4, 13.0, 13.6, 15.5, 17.6, 17.8, 19.2, 20.2, 22.8 and 26.0, or
(8) 6.5, 9.3, 10.5, 12.0, 12.4, 13.0, 13.6, 15.5, 17.6, 17.8, 19.2, 20.2, 22.8, 24.2, 26.0 and 30.7.

Form B may be prepared substantially free of other physical forms by controlled heating of Form A as described in the Examples, or by a slurry technique comprising dissolving, for example, 20% w of a sample of Form A in a suitable solvent (e.g. an organic solvent such as a polar solvent, examples of which include methanol, ethanol, n-propanol, isopropanol and acetone) to form a suspension and homogenising the suspension at ambient temperature (e.g. 20° C.) for at least 7 days, or by dissolving Form A and benzoic acid in a suitable solvent (e.g. heated isopropanol) to form a mixture, allowing the mixture to cool to ambient temperature and periodically seeding the mixture with crystals of Form B.

Where reference is made in this specification to either Form A or Form B being substantially free of other physical forms (or substantially pure), this means that preferably at least 90% by weight, e.g. 90, 91, 92, 93, 94, 95, 96, 97, 98, 99 or 100% w, of the benzoate salt present is in that physical form.

Table 1 below provides further crystallographic data on Forms A and B of the benzoate salt as determined at room temperature.

TABLE 1

|  | Form A | Form B |
| --- | --- | --- |
| Crystal System | Monoclinic | Orthorhombic |
| Dimensions and angle of elementary cell | | |
| a (Å) | 10.82 ± 0.02 | 10.293 ± 0.002 |
| b (Å) | 10.064 ± 0.012 | 10.733 ± 0.002 |
| c (Å) | 14.65 ± 0.03 | 27.447 ± 0.008 |
| α (°) | 90.00 | 90.00 |
| β (°) | 97.86 ± 0.06 | 90.00 |
| γ (°) | 90.00 | 90.00 |

The compounds of the invention are useful as modulators of CCR1 or MIP-1α chemokine receptor activity [N-{2-[((2S)-3-{[1-(4-chlorobenzyl)piperidin-4-yl]amino}-2-hydroxy-2-methylpropyl)oxy]-4-hydroxyphenyl}acetamide ditrifluoroacetate has an IC50 of below 50 nM in the Human CCR1 binding assay such as that described in the Example section herein] and may be administered to a mammal, including man, for the treatment of autoimmune, inflammatory, proliferative and hyperproliferative diseases and immunologically-mediated diseases.

Examples of these conditions are:

1. respiratory tract: obstructive diseases of the airways including: asthma, including bronchial, allergic, intrinsic, extrinsic, exercise-induced, drug-induced (including aspirin and NSAID-induced) asthma, chronic or inverterate asthma (e.g. late asthma and airways hyper-responsiveness), and dust-induced asthma, both intermittent and persistent and of all severities, and other causes of airway hyper-responsiveness; chronic obstructive pulmonary disease (COPD), such as irreversible COPD; bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute, allergic, atropic rhinitis and chronic rhinitis including rhinitis caseosa, hypertrophic rhinitis, rhinitis purulenta, rhinitis sicca and rhinitis medicamentosa, and vasomotor rhinitis; membranous rhinitis including croupous, fibrinous and pseudomembranous rhinitis and scrofoulous rhinitis; perennial and seasonal (allergic) rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies; and Reiter's disease;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions; bullous Pemphigus; uveitis and vernal conjunctivitis;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes; systemic lupus, erythematosus; lepromatosous leprosy; type I diabetes, nephrotic syndrome;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung (e.g. non-small cell lung cancer (NSCLC), ovarian, pancreatic, bowel and colon, stomach, skin and brain tumors, and squamous sarcoma, and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Thus, the present invention provides N-{2-[((2S)-3-{[1-(4-chlorobenzyl)piperidin-4-yl]amino}-2-hydroxy-2-methylpropyl)oxy]-4-hydroxyphenyl}acetamide benzoate or a solvate thereof for use in therapy.

In a further aspect, the present invention provides the use of N-{2-[((2S)-3-{[1-(4-chlorobenzyl)piperidin-4-yl]amino}-2-hydroxy-2-methylpropyl)oxy]-4-hydroxyphenyl}acetamide benzoate or a solvate thereof in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention also provides a method of treating an inflammatory disease in a patient suffering from, or at risk of, said disease, which comprises administering to the patient a therapeutically effective amount of N-{2-[((2S)-3-{[1-(4-chlorobenzyl)piperidin-4-yl]amino}-2-hydroxy-2-methylpropyl)oxy]-4-hydroxyphenyl}acetamide benzoate or a solvate thereof.

The invention still further provides a method of treating an airways disease, e.g. a reversible obstructive airways disease, in a patient suffering from, or at risk of, said disease, which comprises administering to the patient a therapeutically effective amount of N-{2-[((2S)-3-{[1-(4-chlorobenzyl)piperidin-4-yl]amino}-2-hydroxy-2-methylpropyl)oxy]-4-hydroxyphenyl}acetamide benzoate or a solvate thereof.

For the above-mentioned therapeutic uses the dosage administered will, of course, vary with the mode of administration, the treatment desired and the disorder indicated but may typically be in the range from 0.001 mg/kg to 30 mg/kg.

The benzoate salt or solvate thereof according to the invention may be used on its own but will generally be administered in the form of a pharmaceutical composition in which the benzoate salt or solvate thereof (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition may comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising N-{2-[((2S)-3-{[1-(4-chlorobenzyl)piperidin-4-yl]amino}-2-hydroxy-2-methylpropyl)oxy]-4-hydroxyphenyl}acetamide benzoate or a solvate thereof in association with a pharmaceutically acceptable adjuvant, diluent or carrier.

The invention further provides a process for the preparation of a pharmaceutical composition of the invention which comprises mixing N-{2-[((2S)-3-{[1-(4-chlorobenzyl)piperidin-4-yl]amino}-2-hydroxy-2-methylpropyl)oxy]-4-hydroxyphenyl}acetamide benzoate or a solvate thereof with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

In an embodiment of the invention, the benzoate salt of the invention is administered by inhalation. In a further embodiment, the benzoate salt of the invention is administered by means of a dry powder inhaler. The inhaler may be a single or a multi dose inhaler, and may be a breath actuated dry powder inhaler.

When administered via inhalation the dose of the compound (i.e. benzoate salt) of the invention may generally be in the range of from 0.1 µg to 10000 µg, 0.1 to 5000 µg, 0.1 to 1000 µg, 0.1 to 500 µg, 0.1 to 200 µg, 0.1 to 200 µg, 0.1 to 100 µg, 0.1 to 50 µg, 5 µg to 5000 µg, 5 to 1000 µg, 5 to 500 µg, 5 to 200 µg, 5 to 100 µg, 5 to 50 µg, 10 to 5000 µg, 10 to 1000 µg, 10 to 500 µg, 10 to 200 µg, 10 to 100 µg, 10 to 50 µg, 20 to 5000 µg, 20 to 1000 µg, 20 to 500 µg, 20 to 200 µg, 20 to 100 µg, 20 to 50 µg, 50 to 5000 µg, 50 to 1000 µg, 50 to 500 µg, 50 to 200 µg, 50 to 100 µg, 100 to 5000 µg, 100 to 1000 µg or 100 to 500 µg.

Dry powder formulations and pressurized HFA aerosols of the compounds of the invention may be administered by oral or nasal inhalation. For inhalation, the compound is desirably finely divided. The finely divided compound preferably has a mass median diameter of less than 10 µm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

One possibility is to mix the finely divided compound of the invention with a carrier substance, for example, a mono-, di- or polysaccharide, a sugar alcohol, or another polyol.

Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethyl-cellulose as a thickening agent or other excipients known to those skilled in art.

The compounds of the invention may also be administered in conjunction with other compounds used for the treatment of the above conditions.

The invention therefore further relates to combination therapies wherein a compound of the invention or a pharmaceutical composition or formulation comprising a compound of the invention is administered concurrently or sequentially or as a combined preparation with another therapeutic agent or agents, for the treatment of one or more of the conditions listed.

The present invention will now be further explained by reference to the following illustrative examples.

GENERAL METHODS $^1$H NMR spectra were recorded at 298K on a Varian Unity Inova 400 MHz (software: VNMR 6.1C and VNMRJ 1.1D; probe: Nalorac 5 mm DG400-5AT) or a Varian Mercury-VX 300 MHz (software: VNMR 6.1C; probe: Varian 5 mm AutoSW PFG) instrument. The central peaks of acetone-d$_6$ or dimethylsulphoxide (DMSO)-d$_6$ were used as internal references.

The following method was used for LC/MS analysis:

| | |
|---|---|
| MS Instrument: | Agilent 1100 series, equipped with APCI interface |
| LC instrument: | Agilent 1100 series, equipped with UV-detector VWD, autosampler ALS, binary pump and degasser |
| LC-column: | Chromolith Speed ROD, RP-C18, ø 4.6 × 50 mm |
| Eluant: | Solvent A: water + 0.1% trifluoroacetic acid (TFA); Solvent B: acetonitrile + 0.1% TFA |
| Conditions | LC: flow 2.5 ml/minute; 5 to 95% B in gradient; run time 3.6 minutes; UV 220 nm MS: positive detection; capillary voltage 3 kV |

Example 1

Preparation of N-{2-[((2S)-3-{[1-(4-chlorobenzyl)piperidin-4-yl]amino}-2-hydroxy-2-methylpropyl)oxy]-4-hydroxyphenyl}acetamide benzoate (1:1 salt), Form A (a) Hot solutions of N-{2-[((2S)-3-{[1-(4-chlorobenzyl)piperidin-4-yl]amino}-2-hydroxy-2-methylpropyl)oxy]-4-hydroxyphenyl}acetamide (which may be prepared by processes described in WO 03/051839, or by processes analogous to those disclosed in WO 01/98273; 462 mg, 1.0 mmol) in ethyl acetate (10 ml) and benzoic acid (244 mg, 2.0 mmol) in ethyl acetate (10 ml) were mixed. The resulting mixture was left to cool down to ambient temperature (20° C.) in a closed vial. A white precipitate was formed without turbidity. After standing at ambient temperature overnight the precipitate obtained was washed with ethyl acetate (3×10 ml) and dried in vacuo at 60° C. overnight to give the titled salt as an off-white solid (506 mg, 86%). The salt contained traces of ethyl acetate.

$^1$H NMR (399.99 MHz, acetone-d$_6$) δ 8.77 (s, 1H), 8.07-8.04 (m, 2H), 7.83 (d, J=8.7 Hz, 1H), 7.55-7.50 (m, 1H), 7.46-7.41 (m, 2H), 7.36-7.31 (m, 4H), 6.52 (d, J=2.6 Hz, 1H), 6.40 (dd, J=8.7, 2.6 Hz, 1H), 3.97 (d, J=9.3 Hz, 1H), 3.89 (d, J=9.3 Hz, 1H), 3.48 (s, 2H), 3.29 (d, J=12.1 Hz, 1H), 2.94 (d, J=12.2 Hz, 1H), 2.91-2.77 (m, 3H), 2.09-2.00 (m, 4H), 1.98 (s, 3H), 1.72-1.59 (m, 2H), 1.30 (s, 3H)

APCI-MS: m/z 462 [MH+]

The stoichiometry, base to acid, of 1:1 was confirmed by NMR.

Further quantities of the titled salt were prepared by the following method:

(b) Hot solutions of N-{2-[((2S)-3-{[1-(4-chlorobenzyl)piperidin-4-yl]amino}-2-hydroxy-2-methylpropyl)oxy]-4-hydroxyphenyl}acetamide (4.0 g, 8.65 mmol) in ethyl acetate (75 ml) and benzoic acid (1.16 g, 9.5 mmol) in ethyl acetate (75 ml) were mixed. When the resulting mixture had cooled down to ambient temperature (20° C.) it was seeded with a particle of the titled salt obtained in (a) above and was left overnight in a closed flask. The precipitate obtained was washed with ethyl acetate (3×50 ml) and dried in vacuo at 60° C. overnight to give the titled salt as an off-white solid (4.41 g, 87%). The salt contained traces of ethyl acetate.

Example 2

Preparation of N-{2-[((2S)-3-{[1-(4-chlorobenzyl)piperidin-4-yl]amino}-2-hydroxy-2-methylpropyl)oxy]-4-hydroxyphenyl}acetamide benzoate (1:1 salt), Form B (a) The benzoate salt prepared by the method of Example 1(b) (Form A, 10 to 15 mg) was placed in a Differential Scanning Calorimetry pan (with a lid crimped) and using a heating rate of 5 K.min-1, heated until a temperature of 155° C. was reached. Once the salt had melted (an onset melting temperature of 146.5° C. was recorded under the conditions used), the melted sample was cooled down at a rate of 5 K.min-1 to ambient temperature (20° C.). Then the same pan was heated again at a heating rate of 5 K.min-1 until a temperature of 151° C. was reached and the scan recorded an isotherm at 148° C. over a 10 minute period. The pan was then cooled rapidly to ambient temperature resulting in the formation of crystals which were subsequently confirmed by X-ray powder diffraction (XRPD) to be a new physical form of N-{2-[((2S)-3-{[1-(4-chlorobenzyl)piperidin-4-yl]amino}-2-hydroxy-2-methylpropyl)oxy]-4-hydroxyphenyl}acetamide benzoate (Form B). Some amorphous benzoate salt may be formed as a by-product of the process.

(b) The Form B salt described in (a) above was also prepared by dissolving, in a vial, 20% w of a sample of the benzoate salt prepared by the method of Example 1(b) (Form A) in a solvent such as methanol (>20 mg/ml), ethanol (>20 mg/ml), n-propanol (>20 mg/ml), isopropanol (8.5 mg/ml) or acetone (9.6 mg/ml). The figures in brackets indicate the estimated solubility of the salt in these solvents. The vial was then sealed and the suspension was homogenised at ambient temperature (20° C.) using a magnet. Stirring and temperature were maintained for a period of at least 7 days after which time a sample of the material obtained was dried and tested by XRPD. XRPD confirmed that there had been complete transformation of Form A to Form B.

(c) The Form B salt described in (a) above was also prepared by dissolving benzoate salt prepared by the method of Example 1(b) (Form A) (22.0 g, 37.7 mmol) and benzoic acid (0.46 g, 3.8 mmol) in hot 2-propanol (190 ml) in a round-bottomed flask to give a reddish solution. The flask was rotated using a Rotavapor device on a waterbath at 40° C. until the solution had cooled down to 40° C., whereupon it was seeded with some crystals of the Form B salt. The waterbath was allowed to cool down slowly to ambient temperature overnight while the flask was rotating and the mixture was seeded occasionally with some crystals of the Form B salt. A pink precipitate which formed was isolated by suction, washed with 2-propanol (2×50 ml) and dried in vacuo at 100° C. for 20 hours to give the titled salt (as confirmed by XRPD) as a pale pink solid (18.5 g, 84%). The salt contained traces of 2-propanol.

$^1$H NMR (299.95 MHz, DMSO-d6) δ 8.87 (s, 1H), 7.96-7.91 (m, 2H), 7.59-7.52 (m, 1H), 7.49-7.47 (m, 1H), 7.46-7.42 (m, 2H), 7.36 (d, J=8.6 Hz, 2H), 7.29 (d, J=8.6 Hz, 2H), 6.39 (d, J=2.5 Hz, 1H), 6.29 (dd, J=8.5, 2.5 Hz, 1H), 3.78-3.72 (m, 2H), 3.41 (s, 2H), 2.79-2.66 (m, 4H), 1.98 (s, 3H), 1.97-1.88 (m, 2H), 1.85-1.76 (m, 2H), 1.41-1.25 (m, 2H), 1.19 (s, 3H)

APCI-MS: m/z 462 [MH+]

The stoichiometry, base to acid, of 1:1 was confirmed by NMR

Example 3

X-Ray Powder Diffraction Analyses

General Procedures

X-ray powder diffraction (XRPD) analyses may be performed on samples prepared according to standard methods (see for example Giacovazzo et al., eds., Fundamentals of Crystallography, Oxford University Press (1992); Jenkins & Snyder, eds., Introduction to X-Ray Powder Diffractometry, John Wiley & Sons, New York (1996); Bunn, ed., Chemical Crystallography, Clarendon Press, London (1948); and Klug & Alexander eds., X-ray Diffraction Procedures, John Wiley & Sons, New York (1974)).

X-ray powder diffraction patterns of the Form A and Form B salts described in Examples 1 and 2 above (in anhydrous form) were obtained as described below:

A Bragg-Brentano parafocusing powder X-ray diffractometer using monochromatic CuKα radiation (45 kV and 40 mA) was used for the analyses. The primary optics contained soller slits and an automatic divergence slit. Flat samples were prepared on zero background plates that were rotated during the measurements. The secondary optics contained soller slits, an automatic anti scatter slit, a receiving slit and a monochromator. The diffracted signal was detected with a proportional xenon-filled detector. Diffraction patterns were collected between 2°≦2θ (theta)≦40° in a continuos scan mode with a step size of 0.016° 2θ at a rate of 4° 2θ per minute. Raw data were stored electronically. Evaluation was performed on raw or smoothed diffraction patterns.

A Panalytical X'pert PRO MPD θ-θ diffractometer in reflection mode was used for the above-mentioned measurements. A person skilled in the art can set up instrumental parameters for a powder X-ray diffractometer so that diffraction data comparable to the data presented can be collected.

Figure 1:
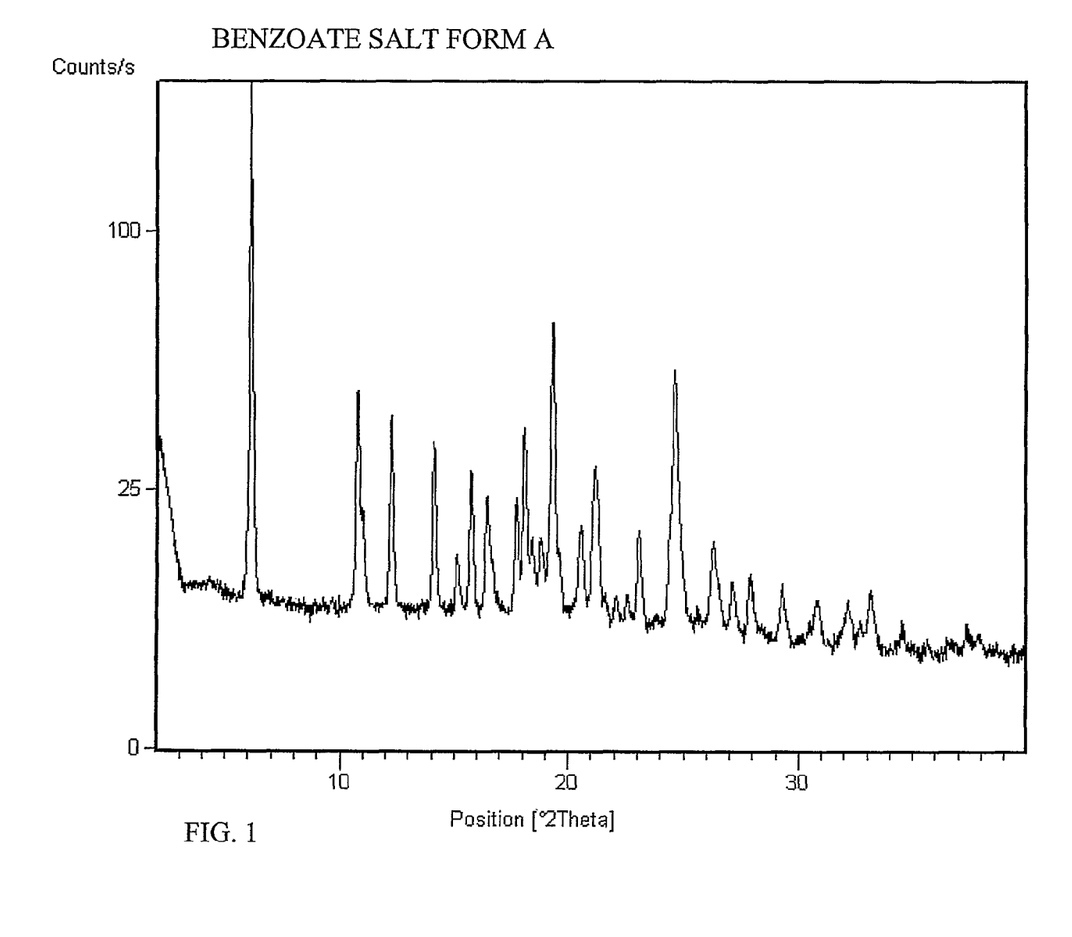
FIG. 1 shows an X-ray powder diffraction pattern of N-{2-[((2S)-3-{[1-(4-chlorobenzyl)piperidin-4-yl]amino}-2-hydroxy-2-methylpropyl)oxy]-4-hydroxyphenyl}acetamide benzoate (Form A).
Figure 2:
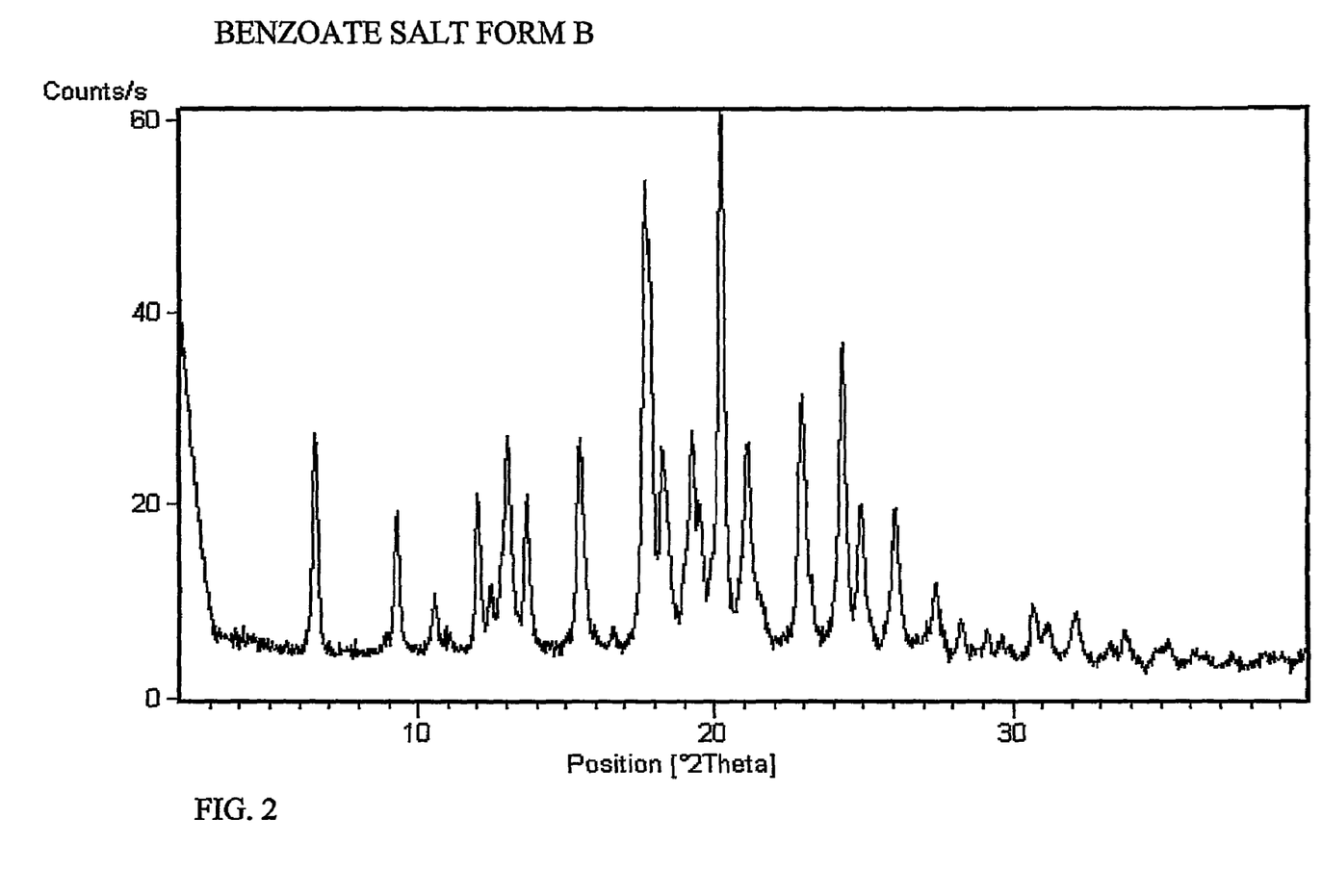
FIG. 2 shows an X-ray powder diffraction pattern of N-{2-[((2S)-3-{[1-(4-chlorobenzyl)piperidin-4-yl]amino}-2-hydroxy-2-methylpropyl)oxy]-4-hydroxyphenyl}acetamide benzoate (Form B).
Figure 3:
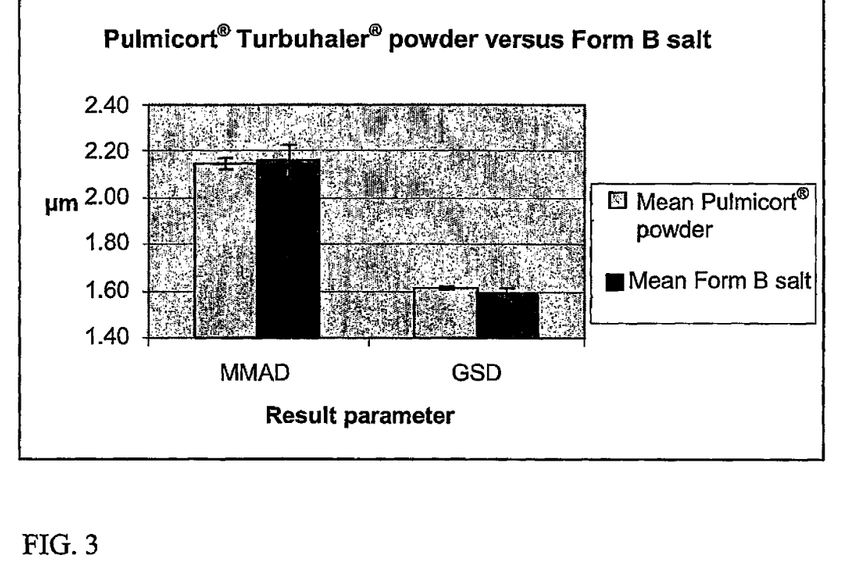
FIG. 3 shows the mass median aerodynamic diameter (MMAD) and geometric standard deviation (GSD) of micronised N-{2-[((2S)-3-{[1-(4-chlorobenzyl)piperidin-4-yl]amino}-2-hydroxy-2-methylpropyl)oxy]-4-hydroxyphenyl}acetamide benzoate (Form B) and Pulmicort® Turbuhaler® formulation, as described in the examples. Error bars are CI95%.
Figure 4:
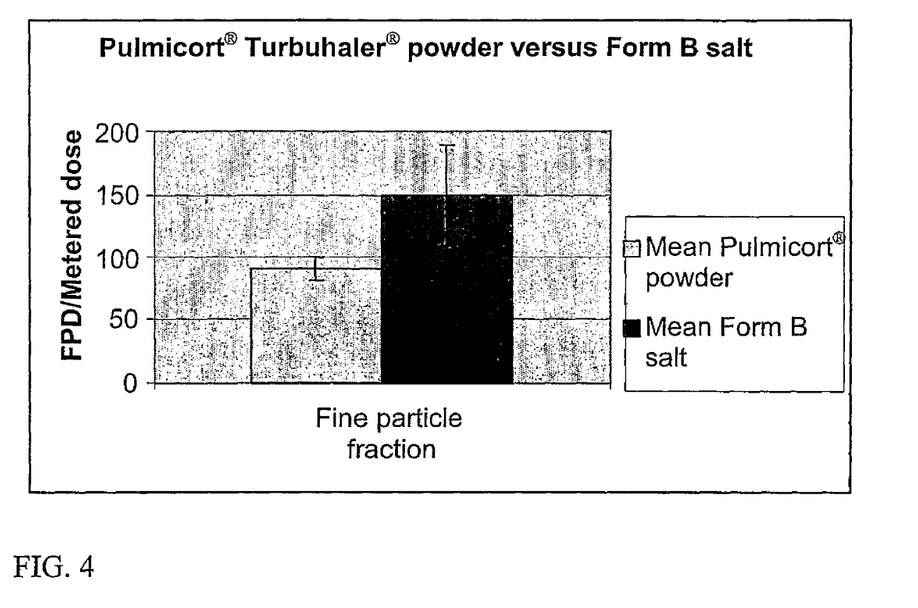
FIG. 4 shows the fine particle fraction (FPF) of micronised N-{2-[((2S)-3-{[1-(4-chlorobenzyl)piperidin-4-yl]amino}-2-hydroxy-2-methylpropyl)oxy]-4-hydroxyphenyl}acetamide benzoate (Form B) and Pulmicort Turbuhaler® formulation, as described in the examples. Error bars are CI95%.

The results obtained are shown in FIG. 1 and FIG. 2.

Example 4

Differential Scanning Calorimetry (DSC)

Using standard methods, for example those described in Höhne, G. W. H. et al (1996), Differential Scanning Calorimetry, Springer, Berlin, the calorimetric response of a test sample to increasing temperature was investigated using a Q1000 Modulated Temperature Differential Scanning Calorimeter (MTDSC) in "heat only" mode with a ramp rate of 5° C. per minute. Approximately 2 to 5 mg of test sample was placed in aluminium cups with lids (no crimping) under a nitrogen atmosphere.

It is well known that the DSC onset and peak temperatures may vary due to the purity of the sample and instrumental parameters, especially the temperature scan rate. A person skilled in the art can use routine optimization/calibration to set up instrumental parameters for a differential scanning calorimeter so that data comparable to the data presented here can be collected.

The melting temperature for a typical sample of the anhydrous Form A salt was found to be 146° C.±2° C. (onset).

The melting temperature for a typical sample of the anhydrous Form B salt was found to be 154° C.±2° C. (onset).

Example 5

Hygroscopicity Determination

The weight change of a test sample at room temperature (25° C.) and at 80% relative humidity (RH) were investigated by recording adsorption-desorption isotherms using a symmetric vapor-sorption analyser SGA-100 (VTI Corporation) using different methods, the main features being: a single sorption/desorption cycle from 0 to 90% RH in 10% RH steps with a dm/dt trigger value of 0.002%, (dm/dt=change in mass with time—when the balance stability is within this value the next step is automatically started, however, if those conditions are not achieved there is a default maximum time for each step of 6 hours). Approximately 2 to 10 mg of the test sample was placed in a sample holder and exposed to different relative humidities.

| Test Sample | Water Uptake (% w/w) at 80% RH |
|---|---|
| Anhydrous Form A | <2 |
| Anhydrous Form B | <0.8 |

Example 6

Evaluation of the Deaggregation Properties of Micronised Salt

Method

This screening study was intended to give some estimation regarding the deaggregation properties of anhydrous N-{2-[((2S)-3-{[1-(4-chlorobenzyl)piperidin-4-yl]amino}-2-hydroxy-2-methylpropyl)oxy]-4-hydroxyphenyl}acetamide benzoate salt, form B (referred to in the remainder of this example as "Form B salt". The results were compared to the results from an established product powder, the Pulmicort® Turbuhaler® formulation, which was tested identically.

Form B salt was micronised in order to obtain a particle size of less than 5 µM. Pulmicort® Turbuhaler® powder was emptied from the Pulmicort® Turbuhaler®. The latter formulation consists of micronised Budesonide powder that is spheronised into small pellets. The micronization of the Form B salt was performed in a spiral jet mill. Within the inner annular space of the jet mill there is a spiral classification. Fine particles will pass through this classification zone and out through a cyclone at the bottom of the mill. The fraction captured in the exhaust filter of the mill was discarded.

For deaggregation of the powders (both for Pulmicort® Turbuhaler® formulation and the Form B salt), the powders were scrape filled into a simple inhaler device comprising an L-shaped cylindrical channel, comprising a vertical component and a horizontal component.

A Turbuhaler® mouthpiece was fastened to the end of the horizontal component to promote deaggregation of the powder, and the powder to be tested was placed via the vertical channel into the bend of the channel (i.e. the corner of the L-shaped channel). An airflow pulse (see below) then activated the airflow through the vertical component of the channel, entraining the powder located in the bend, and the air-particle mixture is thereafter moved through the horizontal component of the cylinder and finally passed through the Turbuhaler® mouthpiece.

After leaving the Turbuhaler® mouthpiece, the aerosol was transferred to a TSI Aerodynamic Particle Sizer (APS®) with Impactor Inlet 3306 set-up where the aerosol cloud was analysed for its aerodynamic properties and fine particle fraction. The APS set-up was arranged in such a way as to allow withdrawal of doses at optional airflows, followed by counting and aerodynamic classification (ca. 0.3-20 μm) of the particles on a particle by particle basis. Briefly, between the USP throat and the 3306 Impacter Inlet, a three-way pneumatic valve and an NGI pre-separator was positioned. In addition, a tube to a vacuum source via a timer-controlled solenoid valve (Triggor Box) was positioned between the valve and the pre-separator in a T-joint fashion. A short airflow pulse is then generated through the inhaler, USP throat, and pre-separator using the Triggor box. After the end of the air pulse, the pneumatic valve switches so that the aerosol cloud in the pre-separator is drawn into the APS via the 3306 Impacter Inlet for aerodynamic assessment.

Each dose was withdrawn with an airflow pulse of duration 0.4 seconds with maximum airflow at 60 lpm, followed by sampling into the APS instrument. The sampling time in the APS software was set to 20 seconds. The result parameters from the APS were mass median aerodynamic diameter (MMAD), geometric standard deviation (GSD), and a measure of the dose amount (particle counting data converted to mass data using particle density=1) called fine particle dose (FPD).

The two first doses (for each formulation) were released and measured gravimetrically. The mean value of these gravimetric doses, denoted "metered doses" or loaded dose, were used for normalisation of the (FPD), which gives a measure of the fine particle fraction (FPF). The FPF can therefore be used for direct comparison between the two powder formulations (for the instrument set up used). The limit for fine particles was set to an aerodynamic particle size of 7 μm. Seven and five doses were then analysed with the APS for Pulmicort® Turbuhaler® formulation and for Form B salt, respectively.

Results

The results are shown in Table 2. The fine particle fraction is FPD divided by metered dose, which in turn is the arithmetic mean of two measurements for each formulation.

The results are plotted in FIG. 3 (MMAD and GSD) and in FIG. 4 (FPF). MMAD and GSD results show very small variability (small confidence intervals) and the difference between the two formulations regarding these two parameters is very small and can more or less be regarded as equivalent.

For the FPF, a larger variability was obtained for Form B salt, which may be attributed to the fact that the powder is not optimised regarding filling properties. However, it was surprisingly noted that the FPF is generally higher for Form B salt than for Pulmicort® Turbuhaler® formulation, which also is reflected in the normalized FPF for the Form B salt.

TABLE 2

Result data. Doses 1-7 are Pulmicort ® Turbuhaler ® data. Dose 8-12 are Form B salt data The normalized Form B salt FPF value[a] is calculated as mean FPF Form B salt/mean FPF Pulmicort ® Turbuhaler ® formulation.

| Dose | FPD/μg | MMAD/ μm | GSD | metered dose/mg | FPF (FPD/ metered dose) |
|---|---|---|---|---|---|
| 1 | 108 | 2.21 | 1.60 | 1.45 | 75 |
| 2 | 134 | 2.15 | 1.60 | 1.45 | 92 |
| 3 | 116 | 2.17 | 1.61 | 1.45 | 80 |
| 4 | 123 | 2.13 | 1.60 | 1.45 | 85 |
| 5 | 139 | 2.11 | 1.62 | 1.45 | 96 |
| 6 | 138 | 2.15 | 1.63 | 1.45 | 95 |
| 7 | 163 | 2.13 | 1.62 | 1.45 | 113 |
| 8 | 167 | 2.28 | 1.54 | 1.22 | 137 |
| 9 | 133 | 2.12 | 1.60 | 1.22 | 109 |
| 10 | 279 | 2.20 | 1.61 | 1.22 | 229 |
| 11 | 157 | 2.10 | 1.60 | 1.22 | 129 |
| 12 | 175 | 2.11 | 1.59 | 1.22 | 144 |
| Mean Pulmicort ® | | | | | |
| Turbuhaler ® formulation | 132 | 2.15 | 1.61 | | 91 |
| Mean Form B salt | 182 | 2.16 | 1.59 | | 149 |
| | | | | Normalized Form B salt | 164%[a] |
| Stdev Pulmicort ® | | | | | |
| Turbuhaler ® formulation | 18.1 | 0.03 | 0.01 | | 12.5 |
| Stdev Form B salt | 56.2 | 0.08 | 0.03 | | 46.1 |
| CI95 Pulmicort ® | | | | | |
| Turbuhaler ® formulation | 13.4 | 0.03 | 0.01 | | 9.3 |
| CI95 Form B salt | 49.3 | 0.07 | 0.02 | | 40.4 |

From the results presented above it can be concluded that the Form B salt formulation displayed a very similar particle size midpoint (MMAD) and particle size distribution (GSD) as the established product formulation (Pulmicort® Turbuhaler® formulation). The fraction of the powder that dispenses into fine particles (fine particle fraction), which is crucial for successful drug delivery to the respiratory tract, was in a similar range for the two different powders, although better for the Form B salt. It is therefore concluded, from the data obtained in this study, that the salt B-formulation displays advantageous de-aggregation properties.

Human CCR1 Binding Assay

Membranes

HEK293 cells, from ECACC, stably expressing recombinant human CCR1 (HEK-CCR1) were used to prepare cell membranes containing CCR1. The membranes were stored at −70° C. The concentration of membranes of each batch was adjusted to 10% specific binding of 33 pM [$^{125}$I] MIP-1α.

Binding Assay

100 μL of HEK-CCR1 membranes diluted in assay buffer pH 7.4 (137 mM NaCl (Merck, Cat No 1.06404), 5.7 mM Glucose (Sigma, Cat No G5400), 2.7 mM KCl (Sigma, Cat No P-9333), 0.36 mM $NaH_2PO_4 \times H_2O$ (Merck, Cat No 1.06346), 10 mM HEPES (Sigma, Cat No H3375), 0.1% (w/v) Gelatine (Sigma, Cat No G2625)) with the addition of 17500 units/L Bacitracin (Sigma, Cat No B 1025) were added to each well of the 96 well filter plate (0.45 μm opaque Millipore cat no MHVB N4550). 12 μL of compound in assay buffer, containing 10% DMSO, was added to give final compound concentrations of $1\times10^{-5.5}$-$1\times10^{-9.5}$ M. 12 μl cold human recombinant MIP-1α (270-LD-050, R&D Systems, Oxford, UK), 10 nM final concentration in assay buffer supplemented with 10% DMSO, was included in certain wells (without compound) as non-specific binding control (NSB). 12 μl assay buffer with 10% DMSO was added to certain wells (without compound) to detect maximal binding (B0).

12 μL [$^{125}$I] MIP-1α, diluted in assay buffer to a final concentration in the wells of 33 pM, was added to all wells. The plates with lid were then incubated for 1.5 hrs at room temperature. After incubation the wells were emptied by vacuum filtration (MultiScreen Resist Vacuum Manifold system, Millipore) and washed once with 200 μl assay buffer. After the wash, all wells received an addition of 50 μL of scintillation fluid (OptiPhase "Supermix", Wallac Oy, Turko, Finland). Bound [$^{125}$I] MIP-1α was measured using a Wallac Trilux 1450 MicroBeta counter. Window settings: Low 5-High 1020, 1-minute counting/well.

Calculation of Percent Displacement and IC$_{50}$

The following equation was used to calculate percent displacement.

Percent displacement=1−((cpm test−cpm NSB)/(cpm B0−cpm NSB)) where:

cpm test=average cpm in duplicate wells with membranes and compound and [$^{125}$I] MIP-1α cpm;
NSB=average cpm in the wells with membranes and MIP-1α and [$^{125}$I] MIP-1α (non-specific binding) cpm;
B0=average cpm in wells with membranes and assay buffer and [$^{125}$I] MIP-1α (maximum binding).

The molar concentration of compound producing 50% displacement (IC$_{50}$) was derived using the Excel-based program XLfit (version 2.0.9) to fit data to a 4-parameter logistics function.

The invention claimed is:

1. A compound being a crystalline Form A of N-{2-[((2S)-3-{[1-(4-chlorobenzyl)piperidin-4-yl]amino}-2-hydroxy-2-methylpropyl)oxy]-4-hydroxyphenyl}acetamide benzoate having an X-ray powder diffraction pattern substantially the same as that shown in FIG. 1.

2. A compound according to claim 1 which is anhydrous.

3. A pharmaceutical composition comprising a compound according to claim 1 in association with a pharmaceutically acceptable adjuvant, diluent or carrier.

4. A method of treating an airways disease in a patient suffering from said disease, which comprises administering to the patient a therapeutically effective amount of a compound according to claim 1 or a pharmaceutical composition according to claim 3,
wherein the airways disease is chronic obstructive pulmonary disease or asthma.

5. The method of claim 4, wherein the airways disease is chronic obstructive pulmonary disease.

6. The method of claim 4, wherein the airways disease is asthma.

7. A dry powder formulation comprising a compound according to claim 1 or a pharmaceutical composition according to claim 3.

8. A dry powder inhaler comprising a compound according to claim 1 or a pharmaceutical composition according to claim 3.

9. A compound being a crystalline Form B of N-{2-[((2S)-3-{[1-(4-chlorobenzyl)piperidin-4-yl]amino}-2-hydroxy-2-methylpropyl)oxy]-4-hydroxyphenyl}acetamide benzoate having an X-ray powder diffraction pattern substantially the same as that shown in FIG. 2.

10. A compound according to claim 9 which is anhydrous.

11. A pharmaceutical composition comprising a compound according to claim 9 in association with a pharmaceutically acceptable adjuvant, diluent or carrier.

12. A method of treating an airways disease in a patient suffering from said disease, which comprises administering to the patient a therapeutically effective amount of a compound according to claim 9 or a pharmaceutical composition according to claim 11,
wherein the airways disease is chronic obstructive pulmonary disease or asthma.

13. The method of claim 12, wherein the airways disease is chronic obstructive pulmonary disease.

14. The method of claim 12, wherein the airways disease is asthma.

15. A dry powder formulation comprising a compound according to claim 9 or a pharmaceutical composition according to claim 11.

16. A dry powder inhaler comprising a compound according to claim 9 or a pharmaceutical composition according to claim 11.

* * * * *